(12) United States Patent
Aghili et al.

(10) Patent No.: US 9,344,224 B2
(45) Date of Patent: *May 17, 2016

(54) METHOD AND APPARATUS FOR RELIABLY TRANSMITTING RADIO BLOCKS WITH PIGGYBACKED ACK/NACK FIELDS (71) Applicant: InterDigital Patent Holdings, Inc., Wilmington, DE (US)

(72) Inventors: Behrouz Aghili, Commack, NY (US); Marian Rudolf, Montreal (CA); Prabhakar R. Chitrapu, Blue Bell, PA (US); Stephen G. Dick, Nesconset, NY (US)

(73) Assignee: InterDigital Patent Holdings, Inc., Wilmington, DE (US)

( * ) Notice: Subject to any disclaimer, the term of this patent is extended or adjusted under 35 U.S.C. 154(b) by 251 days.

This patent is subject to a terminal disclaimer.

(21) Appl. No.: 14/070,042

(22) Filed: Nov. 1, 2013

(65) Prior Publication Data

US 2014/0064191 A1    Mar. 6, 2014

Related U.S. Application Data

(63) Continuation of application No. 12/196,385, filed on Aug. 22, 2008, now Pat. No. 8,576,732.

(60) Provisional application No. 60/957,908, filed on Aug. 24, 2007.

(51) Int. Cl.
*H04L 1/16* (2006.01)
*H04L 1/00* (2006.01)
*H04L 1/12* (2006.01)

(52) U.S. Cl.
CPC ............ *H04L 1/1664* (2013.01); *H04L 1/0081* (2013.01); *H04L 1/0086* (2013.01); *H04L 2001/0098* (2013.01); *H04L 2001/125* (2013.01)

(58) Field of Classification Search
CPC ... H04L 1/1664; H04L 1/1671; H04L 5/0055; H04L 1/1861; H04L 1/0073; H04L 72/0413
See application file for complete search history.

(56) References Cited

U.S. PATENT DOCUMENTS 5,101,501 A   3/1992   Gilhousen et al.
5,280,472 A   1/1994   Gilhousen et al.
(Continued)

FOREIGN PATENT DOCUMENTS

EP    1 341 318    9/2003
KR    2005-0071251    7/2005

OTHER PUBLICATIONS

Nokia Siemens Networks et al., "MCS design and undetected error probability for PAN," 3GPP TSG GERAN #35, GP-071268 (Aug. 27-21, 2007).

(Continued)

*Primary Examiner* — Jung Park
(74) *Attorney, Agent, or Firm* — Volpe and Koenig, P.C.

(57) ABSTRACT

A method and apparatus are described. A wireless transmit/receive unit (WTRU) generates data bits and piggybacked acknowledgement/non-acknowledgement (PAN) bits and generates a plurality of symbols based on the data bits and the PAN bits. Each symbol of the plurality of symbols represents a plurality of bits and has a least significant bit (LSB) position, and no PAN bits are present in the LSB position of each of the plurality of symbols. The plurality of symbols are transmitted.

19 Claims, 5 Drawing Sheets

(56) References Cited

U.S. PATENT DOCUMENTS

| | | | |
|---|---|---|---|
| 5,666,348 | A | 9/1997 | Thornberg et al. |
| 6,247,150 | B1 | 6/2001 | Niemela |
| 6,259,744 | B1 | 7/2001 | Lee et al. |
| 6,356,528 | B1 | 3/2002 | Lundby et al. |
| 6,694,135 | B1 * | 2/2004 | Oksala .................. H04W 74/06 455/424 |
| 7,093,178 | B2 | 8/2006 | Kim et al. |
| 7,869,417 | B2 | 1/2011 | Damnjanovic et al. |
| 2005/0135403 | A1 | 6/2005 | Ketchum et al. |
| 2006/0023687 | A1 | 2/2006 | Cheng et al. |
| 2006/0047947 | A1 | 3/2006 | Langworthy et al. |
| 2006/0056421 | A1 | 3/2006 | Zaki |
| 2006/0077947 | A1 | 4/2006 | Kim et al. |
| 2006/0172758 | A1 | 8/2006 | Ishii et al. |
| 2007/0133458 | A1 | 6/2007 | Chandra et al. |
| 2007/0249343 | A1 * | 10/2007 | Olsson .................. H04L 1/1664 455/435.1 |
| 2008/0037466 | A1 | 2/2008 | Ngo et al. |
| 2008/0056303 | A1 | 3/2008 | Sebire et al. |

OTHER PUBLICATIONS

Siemens Networks et al., "Introduction of Fast Ack/Nack Reporting," 3GPP TSG-GERAN Meeting #33, GP-070273 (Feb. 12-16, 2007).
Siemens Networks, "New Coding Schemes for RTTI and FAST ACK/NACK," 3GPP TSG GERAN #32, GP-062109 (Nov. 13-17, 2007).
Telefon AB LM Ericsson, "Bit Swapping for RED HOT A PAN", 3GPP TSG GERAN #36, GP-071952, (Vancouver, Canada, Nov. 12-16, 2007).
Telefon AB LM Ericsson, "Bit swapping for EGPRS PAN," 3GPP TSG GERAN Meeting #36, GP-071777 (Nov. 12-16, 2007).
Telefon AB LM Ericsson, "Bit swapping for EGPRS PAN," 3GPP TSG GERAN Meeting #36, GP-071964 (Nov. 12-16, 2007).
Telefon AB LM Ericsson, "Bit swapping for RED HOT A PAN," 3GPP TSG GERAN Meeting #36, GP-071953 (Nov. 12-16, 2007).
Telefon AB LM Ericsson, "Correction to burst mapping for HUGE A," 3GPP TSG GERAN#38, GP-080665 (May 12-16, 2008).
Telefon AB LM Ericsson, "Correction to burst mapping for HUGE A," 3GPP TSG WG1 GERAN Ad Hoc on EGPRS2/WIDER/MUROS/MCBTS, AHG1-080022 (Apr. 8-11, 2008).
Telefon AB LM Ericsson, "LATRED and EGPRS2," 3GPP TSG-GERAN Meeting #37, GP-080362 (Feb. 18-22, 2008).
Telefon AB LM Ericsson, "PAN bit swapping EGPRS2," 3GPP TSG GERAN#37, GP-080111 (Feb. 18-22, 2008).
Telefon AB LM Ericsson, "Piggybacked Ack/Nack evaluation," 3GPP TSG GERAN #36, GP-071717 (Nov. 12-16, 2007).
Third Generation Partnership Project; "Technical Specification Group GSM/EDGE Radio Access Network; Channel coding (Release 7)", 3GPP TS 45.003 V7.1.0 (Feb. 2007).
Third Generation Partnership Project; "Technical Specification Group GSM/EDGE Radio Access Network; Channel coding (Release 7)", 3GPP TS 45.003 V7.5.0 (May 2007).
Third Generation Partnership Project; "Technical Specification Group GSM/EDGE Radio Access Network; Channel coding (Release 7)", 3GPP TS 45.003 V7.4.0 (Feb. 2008).
Third Generation Partnership Project; "Technical Specification Group GSM/EDGE Radio Access Network; General Packet Radio Service (GPRS); Overall description of the GPRS radio interface; Stage 2 (Release 7)," 3GPP TS 43.064 V7.9.0 (May 2008).
Third Generation Partnership Project; "Technical Specification Group GSM/EDGE Radio Access Network; General Packet Radio Service (GPRS); Overall description of the GPRS radio interface; Stage 2 (Release 7)," 3GPP TS 43.064 V7.5.0 (May 2007).
Third Generation Partnership Project; "Technical Specification Group GSM/EDGE Radio Access Network; Physical layer on the radio path; General description (Release 6)," 3GPP TS 45.001 V6.8.0 (May 2007).
Third Generation Partnership Project; "Technical Specification Group GSM/EDGE Radio Access Network; Physical layer on the radio path; General description (Release 7)," 3GPP TS 45.001 V7.7.0 (Feb. 2008).
Third Generation Partnership Project; "Technical Specification Group GSM/EDGE Radio Access Network; Physical layer on the radio path; General description (Release 7)," 3GPP TS 45.001 V7.4.0 (May 2007).
Third Generation Partnership Project; "Technical Specification Group GSM/EDGE Radio Access Network; Modulation (Release 6)," 3GPP TS 45.004 V6.0.0 (Jan. 2005).
Third Generation Partnership Project; "Technical Specification Group GSM/EDGE Radio Access Network; Modulation (Release 7)," 3GPP TS 45.004 V7.2.0 (Feb. 2008).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) Protocol (Release 5)," 3GPP TS 44.060 V5.19.0 (May 2006).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) protocol (Release 5)," 3GPP TS 44.060 V5.20.0 (Mar. 2008).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) protocol (Release 6)," 3GPP TS 44.060 V6.22.0 (Jun. 2007).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) protocol (Release 6)," 3GPP TS 44.060 V6.24.0 (May 2008).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) protocol (Release 7)," 3GPP TS 44.060 V7.9.0 (Jun. 2007).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) protocol (Release 7)," 3GPP TS 44.060 V7.13.0 (May 2008).
Third Generation Partnership Project; "Technical Specification Group GSM/EDGE Radio Access Network; General Packet Radio Service (GPRS); Mobile Station (MS)—Base Station System (BSS) interface; Radio Link Control/Medium Access Control (RLC/MAC) protocol (Release 8)," 3GPP TS 44.060 V8.1.0 (May 2008).

* cited by examiner

FIG. 5

METHOD AND APPARATUS FOR RELIABLY TRANSMITTING RADIO BLOCKS WITH PIGGYBACKED ACK/NACK FIELDS

CROSS REFERENCES TO RELATED APPLICATIONS

This application is a continuation of U.S. patent application Ser. No. 12/196,385 filed Aug. 22, 2008, which issued on Nov. 5, 2013 as U.S. Pat. No. 8,576,732, which claims the benefit of U.S. Provisional Application No. 60/957,908, filed Aug. 24, 2007, the contents of which are hereby incorporated by reference herein.

TECHNICAL FIELD

This application is related to wireless communications.

BACKGROUND

The Global System for Mobile Communication (GSM) is one of the most widely deployed communication standards for mobile wireless communication. In order to introduce packet-switched technology, general packet radio service (GPRS) was developed by the European Telecommunications Standards Institute (ETSI). One limitation of GPRS is that it does not support voice services. Other issues with GPRS include lack of higher data rates supported as well as poor link adaptation algorithms. Therefore, the third generation partnership project (3GPP) developed a new standard for GSM to support high rate data services, released in 1999 and known as enhanced data rates for GSM evolution (EDGE).

A network configured according to these standards comprises a core network (CN), at least one wireless transmit/receive units (WTRU) attached to a radio access network (RAN), such as the GSM/EDGE radio access network (GERAN). The GERAN comprises a plurality of base transceiver stations (BTSs), each connected to and controlled by a base station controller (BSC). The combination of the BSCs and the corresponding BTSs is realized as the Base Station System (BSS).

The radio link control/medium access control (RLC/MAC) protocol, which resides in the WTRU and the BSS, is responsible for reliable transmission of information between the WTRU and the network. In addition, the physical layer latency, (for example, packet transfer and serialization delays) is controlled by the RLC/MAC protocol.

A goal for GERAN evolution is to develop new technology, new architecture and new methods for settings and configurations in wireless communication systems. One work item for GERAN evolution is latency reduction. Release 7 (R7) of the 3GPP GERAN standard introduces several features that may improve throughput and reduce latency of transmissions in the uplink (UL) and the downlink (DL). UL improvements are referred to as higher uplink performance for GERAN evolution (HUGE), and DL improvements are referred to as reduced symbol duration higher order modulation and turbo coding (REDHOT). Both of these improvements may generally be referred to as evolved general packet radio service 2 (EGPRS-2) features.

The Latency Reduction feature includes two (2) technical approaches that may operate either in a stand-alone mode, or in conjunction with any of the other GERAN R7 improvements. One approach uses a fast positive acknowledgement/negative acknowledgement (ACK/NACK) reporting (FANR) mode. Another approach uses a reduced transmission time interval (RTTI) mode. A WTRU may operate in both FANR and RTTI modes of operation with legacy EGPRS modulation and coding schemes (MCSs), and with the newer EGPRS-2 modulation and coding schemes.

REDHOT and HUGE provide increased data rates and throughput compared to legacy EGPRS DL and UL. These modes may be implemented through the use of higher order modulation schemes, such as sixteen quadrature amplitude modulation (16-QAM) and thirty two quadrature amplitude modulation (32-QAM). These modes may also involve the use of higher symbol rate transmissions and turbo-coding. Similar to legacy systems, REDHOT and HUGE involve an extended set of modulation and coding schemes that define new modified information formats in the bursts, various coding rates and coding techniques and the like.

Prior to the introduction of FANR, ACK/NACK information was typically sent in an explicit message, referred to as an RLC/MAC control block, which contained a starting sequence number and a bitmap representing radio blocks. The reporting strategy (how and when reports are sent, and the like) was controlled by the network. The WTRU would send a Control Block as a response to a poll from the base station system (BSS). The poll will also include information about the UL transmission time (for example, when the WTRU is allowed to send its control block in the UL). During normal operation, when higher layer information is exchanged between the WTRU and the network, the information transfer occurs using RLC Data Blocks.

A drawback of the current ACK/NACK reporting protocols is that a full control block is needed every time ACK/NACK information is sent. Therefore, a large overhead is required when ACK/NACK information is frequently needed for delay sensitive services.

Consequently, within the framework of GERAN evolution, a new ACK/NACK state machine that uses ACK/NACK reports "piggybacked" on RLC Data Blocks in the opposite link direction was introduced.

This protocol has the potential to significantly reduce the retransmission delay without significant overhead. These piggybacked ACK/NACK (PAN) reports are bitmaps, designed as a combination of block sequence numbers (BSNs) which specify outstanding radio blocks bitmaps giving ACK/NACK information of radio blocks, and size bits or extension bits specifying the size of the ACK/NACK information. PANs are used to transmit an ACK/NACK bitmap within a radio block carrying RLC data.

This allows for ACK/NACK information to consist either of one single PAN or to be split into several multiple segment PANs. This allows for a decrease in latency and round-trip times due to increased flexibility of sending ACK/NACK reports independently from data transmissions to a particular wireless transmit/receive unit (WTRU) without necessitating special RLC/MAC control blocks, while maintaining general principles of RLC window operation.

Figure 1:
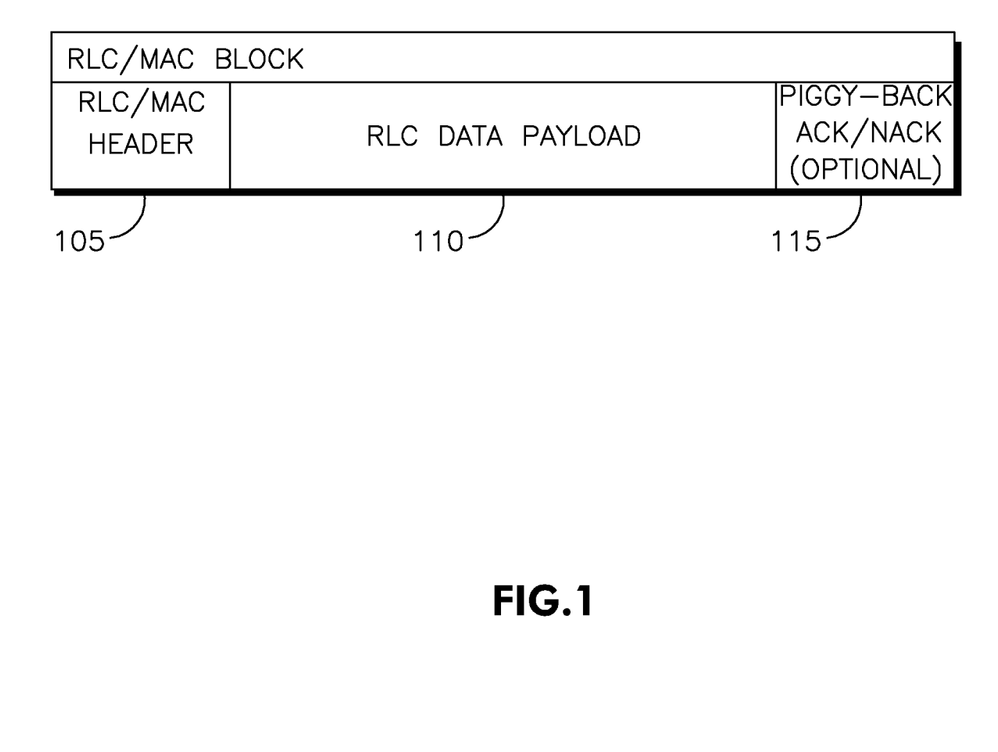
FIG. 1 is a conventional RLC/MAC block structure for EGPRS data transfer.

FIG. 1 shows a conventional radio block. Currently, a PAN field may be inserted into a RLC/MAC radio block using modulation and coding schemes (MCSs) for EGPRS or new MCSs provided by REDHOT/HUGE (EGPRS-2). In both of these scenarios, the radio block consists of a separately encoded RLC/MAC header 105 that is decodable independent from the RLC data payload; an RLC data payload 110 and a PAN field 115 that is separately decodable from the RLC/MAC header and RLC data payload.

Some legacy EGPRS radio blocks and some new RED-HOT/HUGE radio blocks may contain more than one RLC data Protocol Data Unit (PDU) per radio block. The PAN is mapped on the burst together with the data. The placement of the PAN before interleaving is dependent on the interleaving depth of the data block. Since all PANs have low code rates, a maximized interleaving depth is preferred.

The insertion of the PAN field 115 into the radio block requires heavier puncturing of the actual RLC data payload. In essence, since the overall number of bits that may be placed into the radio block is fixed, more encoded data bits must be removed from the RLC data payload once a PAN is inserted. Since the RLC/MAC header coding remains unchanged even when a PAN is inserted, the coding rate of the data portion should be increased. However, this may be detrimental to link performance and effectiveness of the link adaptation algorithm, because the increased channel coding rate and reduced number of channel bits of the affected RLC data payload 110 of the radio block may lead to more transmission errors and less protection of the data.

Another problem is that the RLC/MAC header 105, the RLC data payload 110 and the PAN field 115 are all independently channel coded. For example, a PAN field, which contains M=20 information bits and N=6 cyclic redundancy check (CRC) bits, is coded into 80 channel coded bits yielding a coding rate of approximately 0.33. Therefore, balancing error performance of the RLC/MAC header 105, the RLC data payload 110 and the PAN field 115 is essential to good performance of the radio block.

Figure 2:
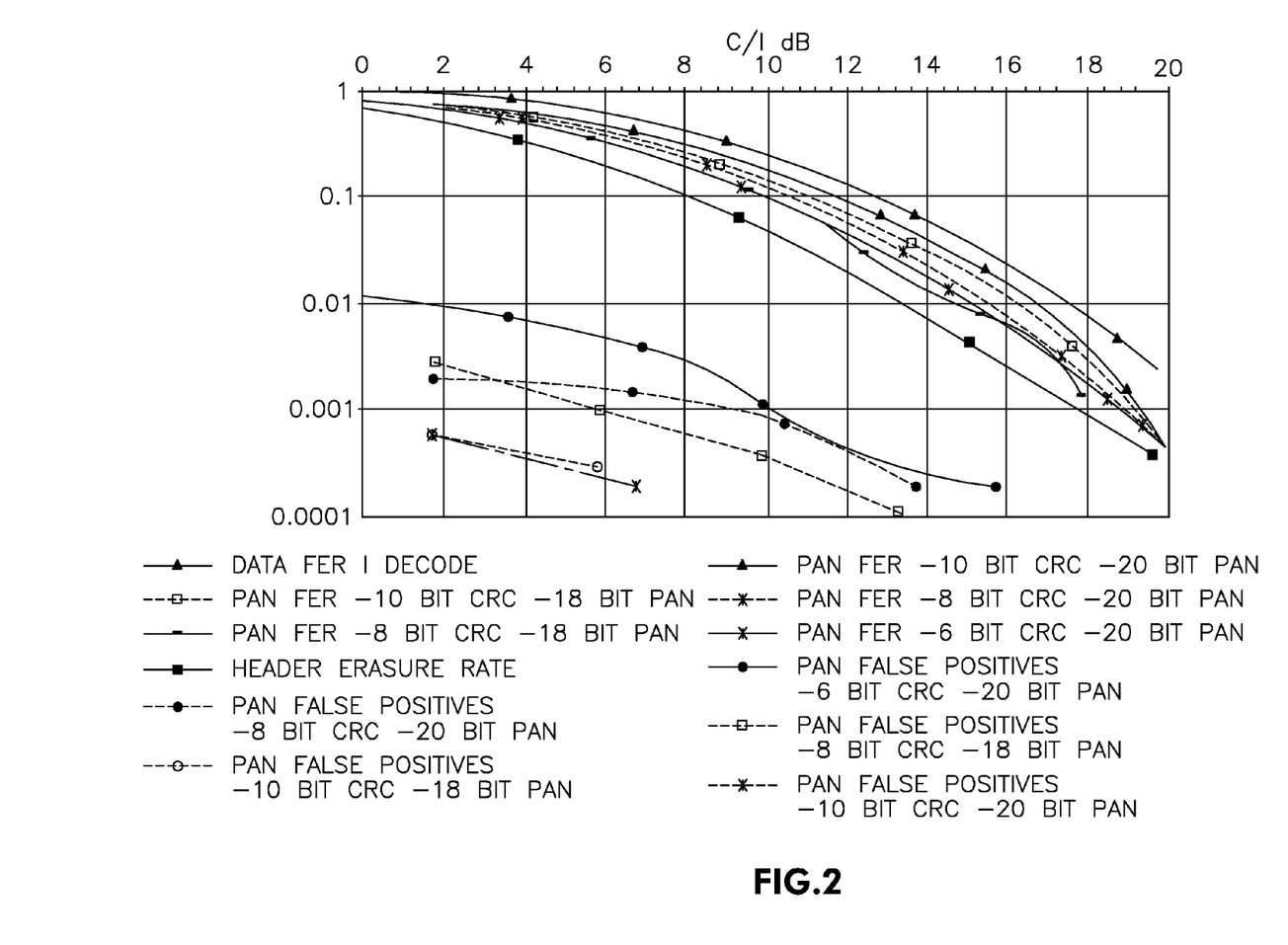
FIG. 2 depicts the error ratios of different portions of a RLC/MAC radio block without bit swapping.

The different error performances of the portions making up the RLC MAC radio block 110 are shown in FIG. 2. For example, if the error rate of the RLC/MAC header 105 becomes too high, more transmissions are lost due to the receiver (WTRU or base station) failing to decode the RLC/MAC header 105, rather than errors in the RLC data payload 110. The protection of the PAN field 115 is also questionable, as well as the mapping of the PAN field 115.

In the conventional RLC/MAC radio block of FIG. 1, the RLC/MAC header 105, the RLC data payload 110 and the PAN field 115 are interleaved together. Their channel-coded bits carried by the modulation symbols are spread across four (4) radio bursts such that bits belonging to the PAN field 115, for example, are not necessarily contiguous. Applying a power offset just to a subset of PAN-carrying symbols may create extra leaking of transmit (Tx) power into the adjacent carriers due to radio frequency (RF) non-linearity from "normal" symbols transiting to symbols sent at higher offset power at the configured standard peak-to-average ratio (PAR) back-off for the given modulation order. This may result in intolerable out-of-band emission levels.

It is therefore desirable to have a method and apparatus for linking performance and error resilience of different portions of a radio block and matching portions of a radio block to their respective requirements for PAN filed inclusion, when compared to transmission without PAN field inclusion, without changing the number of channel coded bits.

SUMMARY

A method and apparatus are described. A wireless transmit/receive unit (WTRU) generates data bits and piggybacked acknowledgement/non-acknowledgement (PAN) bits and generates a plurality of symbols based on the data bits and the PAN bits. Each symbol of the plurality of symbols represents a plurality of bits and has a least significant bit (LSB) position, and no PAN bits are present in the LSB position of each of the plurality of symbols. The plurality of symbols are transmitted.

BRIEF DESCRIPTION OF THE DRAWINGS

A more detailed understanding may be had from the following description, given by way of example and to be understood in conjunction with the accompanying drawings wherein.

DETAILED DESCRIPTION

When referred to herein, the terminology "wireless transmit/receive unit (WTRU)" includes but is not limited to a user equipment (UE), a mobile station, a fixed or mobile subscriber unit, a pager, a cellular telephone, a personal digital assistant (PDA), a computer, or any other type of user device capable of operating in a wireless environment. When referred to herein, the terminology "base station" includes but is not limited to a Node-B, a site controller, an access point (AP), or any other type of interfacing device capable of operating in a wireless environment.

Figure 3:
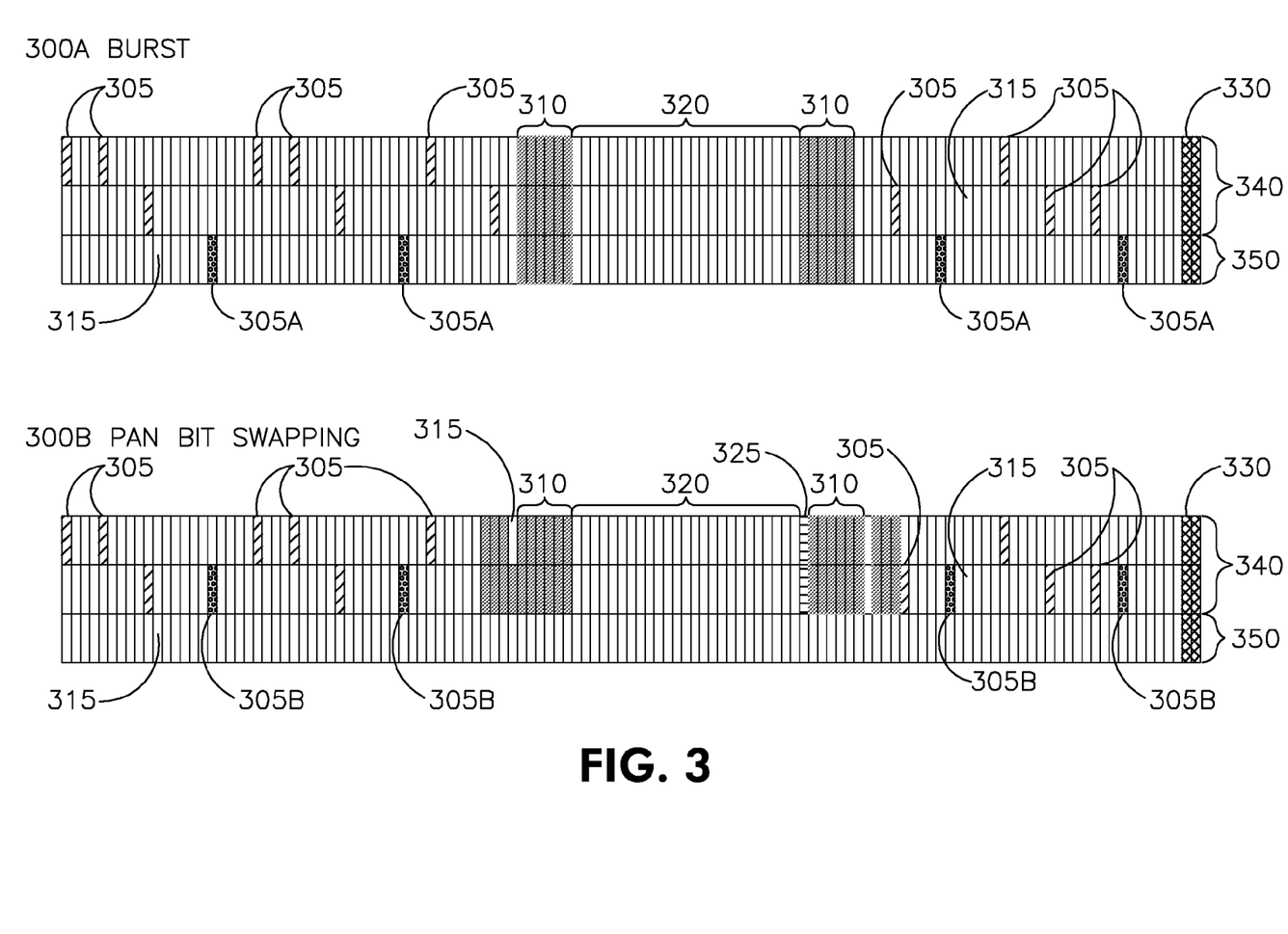
FIG. 3 shows the structure of a radio block without PAN bit swapping compared to the structure of a radio block with PAN bit swapping.

FIG. 3 shows the structure of a burst 300A. The burst 300A includes PAN bits 305, header bits 310, and data bits 315. PAN bits 305 are interspersed throughout the burst and may be found in all bit positions of a symbol. It is noted that while the burst 300A is representative of eight phase shift keying (8-PSK) modulation (that is, three bits per symbol), the PAN bit swapping technique disclosed herein may be applied to any modulation order. Due to the nature of phase shift keying modulation, those skilled in the art will recognize that the third bit position 350 of each symbol is more prone to error than the first two bit positions 340 of each symbol.

FIG. 3 also shows the structure of modulated information bits after PAN bit swapping (300B) is applied, according to one embodiment. PAN bits 305 in unreliable bit positions 350 of the each symbol (in the illustrated case of 8-PSK, the third bit position of each symbol) are "swapped" with data bits 315 in more reliable bit positions 340. For example, PAN bit 305A is shown in burst 300A in the third bit position of a symbol. After PAN bit swapping, PAN bit 305A has been swapped with a data bit 315 from a more reliable bit position. PAN bit 305B is now located in a more reliable position. After channel coding, the burst is also accompanied by a training sequence 320, two stealing flags (SF) 325, and, in the DL direction, an uplink state flag (USF) 330 fields.

It is noted that PAN bit swapping as disclosed herein improves the reliability of PAN bits 305. However, as a trade off, data bits 315 that are swapped with PAN bits 305 are less reliable. Due to the importance of PAN bits 305 and data retransmission techniques, this trade off is generally acceptable.

Additionally, areas in the middle of the burst 300A, such as the training sequence 320, are less prone to bad channel conditions. Therefore, it may be advantageous to swap PAN bits 305 with other bits that are close to the training sequence 320. It would likewise be advantageous to swap PAN bits 305 with other bits in more desirable locations of the radio block.

The PAN bit swapping described with reference to FIG. 3 may also be applied to higher order modulation. More reliable (that is, most significant bits or outer constellation points) of sixteen quadrature amplitude modulation (16-QAM) and thirty two quadrature amplitude modulation (32-QAM) may be used for PAN bit swapping. Of course, PAN bit swapping as disclosed may be used with any modulation technique having multiple bits per symbol.

In addition to PAN bit swapping, one or more power offsets may be applied to one or more individual portions of the burst 300A to improve performance. The power offsets may be applied individually or in combination to the header 310, data 315, PAN 305, training sequence 320, stealing flag (SF) 325, and/or uplink state flag (USF) 330 fields, in order to balance the individual error performance of each of the portions. The power offset or may be adjusted during system operation to take into account varying radio conditions, interference levels, power headroom, or presence and absence of individual fields by the radio transmitter. Accordingly, different power offset values may be applied to the different fields. By selective application of power offsets to certain portions of a radio block, link performance may be increased while creating only minimal interference to other receivers.

Figure 4:
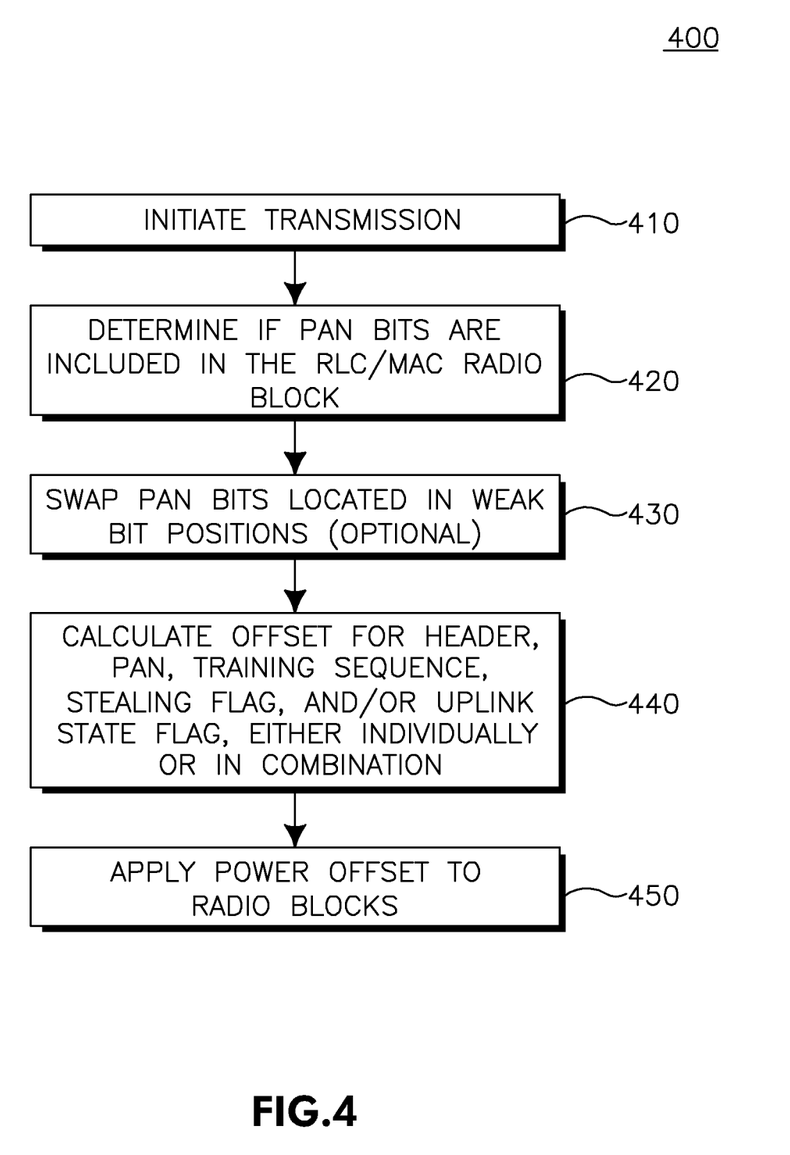
FIG. 4 is a block diagram of a wireless communication system including a WTRU and a base station used to transmit and receive radio blocks with piggybacked ACK/NACK fields.

Referring to FIG. 4, an exemplary method 400 of applying a power offset as described above begins with initiating a transmission, (step 410). It is then determined if PAN bits are included in the radio block, (step 420). Depending on system operation, PAN bits may always be included so this step may be unnecessary. If PAN bits are present, the PAN bits located in unreliable bit positions are swapped with bits in more reliable bit positions, (step 430), as described above. Next, a power offset may be calculated for each various bits and/or regions of the radio block (for example, header field, PAN bits, training sequence, stealing flag), (step 440). Finally, the calculated power offset is applied to the radio block, (step 450).

In the method 400, the calculated power offset may, for example, counter-balance the effect of an increased coding rate for data bits. The calculated power offset may be applied semi-statically, using periodic adjustments, or may be adjusted during system operation to take into account varying radio conditions and/or interference levels and/or power headroom.

A WTRU may independently calculate the power offset values based on predetermined criteria or measured values, or the WTRU may receive power offset values from the network. The network may adjust or configure the offset values based on link adaptation mechanisms. For example, the offset value may be signaled to a WTRU in a separate control block, (for example a packet power control/timing advance, packet time slot reconfigure or packet UL ACK/NACK message). Alternatively, other RLC/MAC control blocks may also be modified to convey this type of information.

When PAN bit swapping and power offsets are used in combination, PAN bits may be swapped with other bits of a single radio burst among the four (4) radio bursts that make up a radio block, and a power offset may be applied to the entire radio burst containing the PAN bits. This approach avoids varying power levels within a burst. Alternatively, the PAN bits may also be swapped with bits of a subset of the four (4) radio bursts that make up the radio block. The power offset may then be applied to the bursts carrying the PAN bits. These methods may also be applied to the other bits, such as the header, data bits, and the like.

Figure 5:
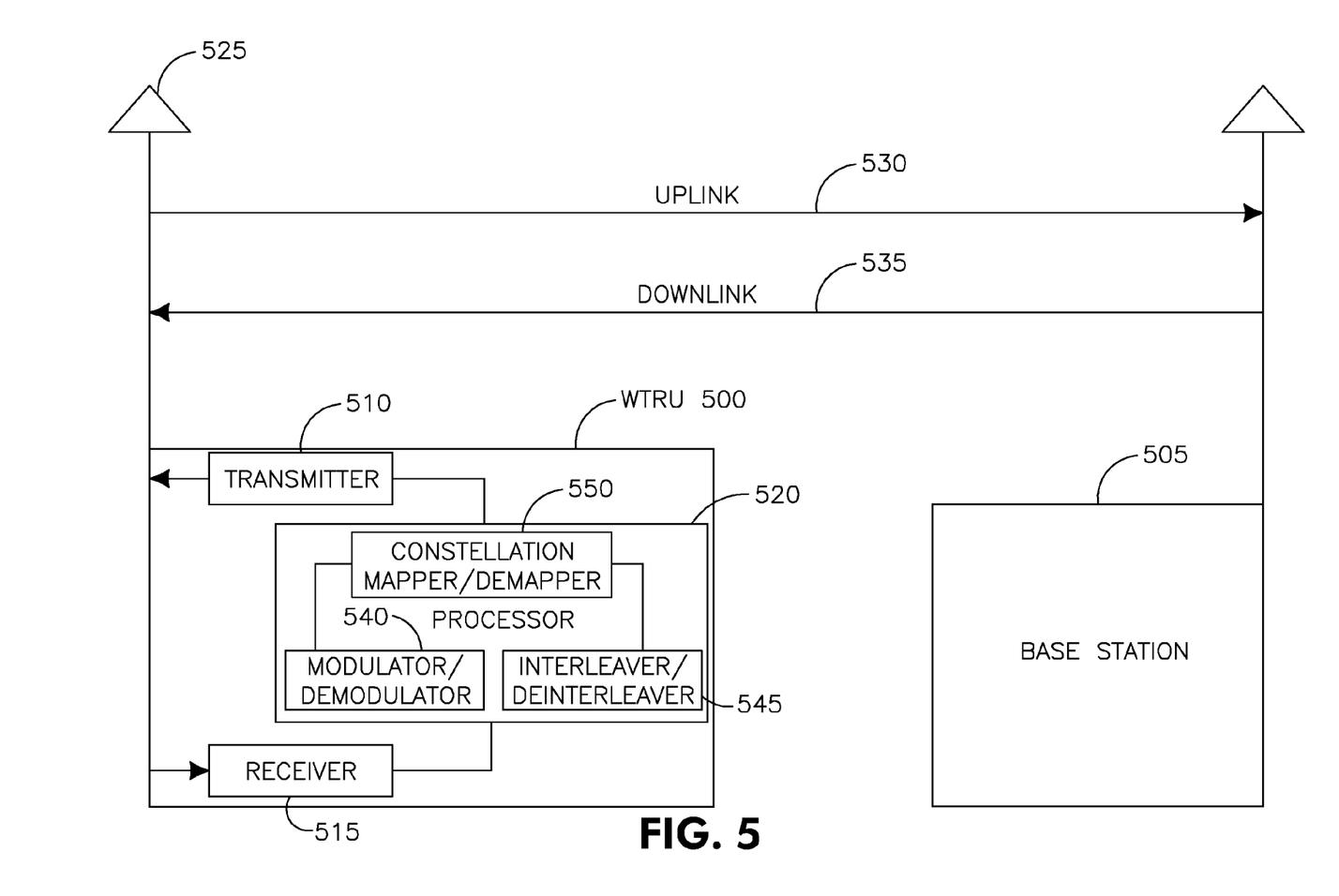
FIG. 5 is a flow diagram of a procedure performed by the WTRU of FIG. 4.

FIG. 5 shows a WTRU 500 and a base station 505 each configured to implement the above disclosed methods. The WTRU 500 includes a transmitter 510, a receiver 515, and a processor 520. The transmitter 510 and receiver 520 are coupled to an antenna 525 and the processor 520. The WTRU 500 communicates with the base station 505 in an uplink direction 530 and a downlink direction 535 via an air interface. The processor 520 includes a modulator/demodulator 540, an interleaver/deinterleaver 545, and a constellation mapper/demapper 550. The processor 520 is configured to produce radio blocks for transmission and process received radio blocks as described above. The interleaver/deinterleaver 545 is configured to interleave and deinterleave bits in a radio block, and to swap PAN bits with data bits as disclosed. The constellation mapper/demapper 550 is configured to code and decode symbols based on a modulation technique, such as QPSK, 16-QAM, 32-QAM, or the like, and to swap PAN bits with data bits as disclosed in cooperation with the interleaver/deinterleaver 545. The modulator/demodulator 540 is configured to modulate the prepared radio block for uplink transmission via the transmitter 510 and to demodulate received radio blocks in the downlink via the receiver 515.

The processor 520 of the WTRU 510 is further configured to apply power offsets to various regions of the radio blocks, as disclosed. The processor 520, in combination with the transmitter 510, may adjust the transmission power according to calculated or received power offset values, either semi-statically or based on changing channel conditions, as described above. The processor 520 is further configured to receive, via the receiver 515, power offset values from the base station 505.

The base station 505 may contain similar functionality as described above with reference to the WTRU 500. A processor of the base station may be configured to generate power offset commands as disclosed, and to swap PAN bits as disclosed.

Although the features and elements are described in the embodiments in particular combinations, each feature or element can be used alone without the other features and elements of the embodiments or in various combinations with or without other features and elements. The methods or flow charts provided in the present invention may be implemented in a computer program, software, or firmware tangibly embodied in a computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. A processor in association with software may be used to implement a radio frequency transceiver for use in a WTRU, user equipment (UE), terminal, base station, radio network controller (RNC), or any host computer. The WTRU may be used in conjunction with modules, implemented in hardware and/or software, such as a camera, a video camera module, a videophone, a speakerphone, a vibration device, a speaker, a microphone, a television transceiver, a hands free headset, a keyboard, a Bluetooth® module, a frequency modulated (FM) radio unit, a liquid crystal display (LCD) display unit, and an organic light-emitting diode.

What is claimed is:

1. A method for use in a base station (BS), the method comprising:
   generating a stream of bits for transmission, the stream of bits including data bits and piggybacked acknowledgement/non-acknowledgement (PAN) bits;
   interleaving the stream of bits to create an interleaved stream of bits;
   modulating the interleaved stream of bits to create a plurality of symbols, wherein each symbol represents a plurality of bits and has a least significant bit (LSB) position, and wherein no PAN bits are present in the LSB position of each of the plurality of symbols; and
   transmitting the plurality of symbols.

2. The method of claim 1, wherein the modulating the stream of bits is performed using eight phase shift keying (8PSK) modulation.

3. The method of claim 1, wherein the modulating the stream of bits is performed using sixteen quadrature amplitude modulation (16-QAM).

4. The method of claim 1, wherein the modulating the stream of bits is performed using thirty two quadrature amplitude modulation (32-QAM).

5. The method of claim 1, wherein the PAN bits are located proximate to a training sequence.

6. The method of claim 1, further comprising applying a power offset value to a transmission power associated with each bit of the stream of bits.

7. The method of claim 6, wherein the stream of bits further includes header bits, stealing flags, training sequence bits, and uplink state flag bits.

8. The method of claim 7, wherein the applied power offset value is based on a type of bit of the bit stream.

9. A base station (BS) comprising:
   a processor configured to generate a stream of bits for transmission, the stream of bits including data bits and piggybacked acknowledgement/non-acknowledgement (PAN) bits;
   an interleaver configured to interleave the stream of bits to create an interleaved stream of bits;
   a modulator configured to modulate the interleaved stream of bits to create a plurality of symbols, wherein each symbol represents a plurality of bits and has a least significant bit (LSB) position, and wherein no PAN bits are present in the LSB position of each of the plurality of symbols; and
   a transmitter configured to transmit the plurality of symbols.

10. The BS of claim 9, wherein the modulator is further configured to modulate the stream of bits using eight phase shift keying (8PSK) modulation.

11. The BS of claim 9, wherein the modulator is further configured to modulate the stream of bits using sixteen quadrature amplitude modulation (16-QAM).

12. The BS of claim 9, wherein the modulator is further configured to modulate the stream of bits using thirty two quadrature amplitude modulation (32-QAM).

13. The BS of claim 9, wherein the PAN bits are located proximate to a training sequence.

14. The BS of claim 9, wherein the transmitter is further configured to apply a power offset value to a transmission power associated with each bit of the stream of bits.

15. The BS of claim 14, wherein the stream of bits further includes header bits, stealing flags, training sequence bits, and uplink state flag bits.

16. The BS of claim 15, wherein the applied power offset value is based on a type of bit of the bit stream.

17. A method for use in a base station (BS), the method comprising:
   generating data bits and piggybacked acknowledgement/non-acknowledgement (PAN) bits;
   generating a plurality of symbols based on the data bits and the PAN bits, wherein each symbol of the plurality of symbols represents a plurality of bits and has a least significant bit position (LSB), and wherein no PAN bits are present in the LSB position of each of the plurality of symbols; and
   transmitting the plurality of symbols.

18. The method of claim 17, wherein the generating the plurality of symbols includes:
   channel coding the data bits and the PAN bits to generate channel-coded bits,
   interleaving the channel-coded bits to generate interleaved bits; and
   modulating the interleaved bits to generate the plurality of symbols.

19. The method of claim 18, wherein the modulating the interleaved bits includes using eight phase shift keying (8PSK) modulation, sixteen quadrature amplitude modulation (16-QAM), or thirty two quadrature amplitude modulation (32-QAM).

* * * * *